(12) United States Patent
Berger et al.

(10) Patent No.: US 9,245,161 B2
(45) Date of Patent: Jan. 26, 2016

(54) METHOD AND SYSTEM FOR COMPUTED RADIOGRAPHY USING A RADIO FREQUENCY IDENTIFICATION DEVICE

(71) Applicant: Carestream Health, Inc., Rochester, NY (US)

(72) Inventors: Amir Berger, Kiryat Bialik (IL); Bruno Ehrmann, Suresnes (FR); Oded Wigderson, Haifa (IL); Dmitry Teif, Nesher (IL); Jean-Marc Inglese, Bussy Saint Georges (FR)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 14/067,156

(22) Filed: Oct. 30, 2013

(65) Prior Publication Data

US 2014/0049380 A1  Feb. 20, 2014

Related U.S. Application Data

(63) Continuation of application No. 12/976,011, filed on Dec. 22, 2010, now abandoned.

(60) Provisional application No. 61/334,331, filed on May 13, 2010.

(51) Int. Cl.
*H04Q 5/22* (2006.01)
*G06K 7/10* (2006.01)
*A61B 6/14* (2006.01)
(Continued)

(52) U.S. Cl.
CPC ............ *G06K 7/10376* (2013.01); *A61B 6/145* (2013.01); *A61B 6/4411* (2013.01); *A61B 6/4494* (2013.01); *G03B 42/047* (2013.01)

(58) Field of Classification Search
None
See application file for complete search history.

(56) References Cited

U.S. PATENT DOCUMENTS

| 1,632,154 A | 6/1927 | Torpin |
| 2,426,286 A | 8/1947 | Stadler |
| 4,344,013 A * | 8/1982 | Ledley .......................... 378/126 |

(Continued)

FOREIGN PATENT DOCUMENTS

| EP | 0 727 696 B1 | 5/2003 |
| JP | 2005-111254 A | 4/2005 |

(Continued)

OTHER PUBLICATIONS

European Search Report dated Jul. 25, 2011 for European Application No. 11 003 996.3, 3 pages.

*Primary Examiner* — Curtis King

(57) ABSTRACT

A method for obtaining an X-ray image of a subject on a flexible information carrier plate for computed radiography. A memory is affixed to a surface of the plate, wherein the affixed memory stores information about the plate and is in wireless communication with a computer. A first scan date is stored in the affixed memory. Obtaining the X-ray image uses steps of storing at least a job identifier and a scan status for the plate in the affixed memory; acquiring image data from a scan of the plate following exposure to X-rays, acquiring at least the job identifier from the affixed memory, and associating the acquired image data with the acquired job identifier; incrementing a scan count value and updating the scan status in the affixed memory; erasing image content from the plate; and storing the acquired image data in a second, computer-accessible memory according to the acquired job identifier.

20 Claims, 12 Drawing Sheets

(51) Int. Cl.
  *A61B 6/00*      (2006.01)
  *G03B 42/04*     (2006.01)

(56)            References Cited

U.S. PATENT DOCUMENTS

| | | | |
|---|---|---|---|
| 4,739,480 | A | 4/1988 | Oono et al. |
| 4,960,994 | A | 10/1990 | Muller et al. |
| 5,136,626 | A | 8/1992 | Ort |
| 5,418,355 | A | 5/1995 | Weil |
| 5,428,659 | A | 6/1995 | Renner et al. |
| 5,748,173 | A | 5/1998 | Gur |
| 5,757,021 | A | 5/1998 | Dewaele |
| 5,950,207 | A | 9/1999 | Mortimore et al. |
| 5,995,138 | A | 11/1999 | Beer et al. |
| 6,033,111 | A | 3/2000 | Winters et al. |
| 6,097,902 | A | 8/2000 | Blumé |
| 6,190,042 | B1 | 2/2001 | Dove et al. |
| 6,359,628 | B1 | 3/2002 | Buytaert |
| 6,381,416 | B2 | 4/2002 | Manico et al. |
| 6,381,418 | B1 | 4/2002 | Spurr et al. |
| 6,826,313 | B2 | 11/2004 | Robar et al. |
| 7,095,034 | B2 | 8/2006 | Haug et al. |
| 7,127,039 | B2 | 10/2006 | Woods |
| 7,211,785 | B1 | 5/2007 | Berger et al. |
| 7,319,396 | B2 | 1/2008 | Homanfar et al. |
| 7,518,518 | B2 | 4/2009 | Homanfar et al. |
| 7,563,025 | B2 | 7/2009 | Kay |
| 7,775,713 | B2 | 8/2010 | Klemola et al. |
| 7,896,229 | B2 | 3/2011 | Crucs et al. |
| 8,152,523 | B2 | 4/2012 | Sporbert et al. |
| 8,177,551 | B2 | 5/2012 | Sachdeva et al. |
| 8,374,461 | B2 | 2/2013 | Humphreys et al. |
| 2004/0011976 | A1 | 1/2004 | Kay |
| 2004/0169149 | A1 | 9/2004 | Alzner et al. |
| 2005/0103840 | A1* | 5/2005 | Boles .......................... 235/385 |
| 2005/0133730 | A1* | 6/2005 | Haug et al. ............... 250/484.4 |
| 2005/0232575 | A1 | 10/2005 | Koren |
| 2006/0133579 | A1 | 6/2006 | Lee et al. |
| 2006/0219964 | A1 | 10/2006 | Mochizuki et al. |
| 2006/0257816 | A1 | 11/2006 | Klemola et al. |
| 2006/0261296 | A1 | 11/2006 | Heath et al. |
| 2008/0240360 | A1* | 10/2008 | Jabri ......................... 378/163 |
| 2009/0212107 | A1* | 8/2009 | Crucs et al. ................ 235/385 |
| 2010/0080345 | A1* | 4/2010 | Schilling et al. ............. 378/37 |
| 2012/0001737 | A1 | 1/2012 | Berger et al. |
| 2012/0019369 | A1* | 1/2012 | Taskinen et al. ......... 340/10.42 |

FOREIGN PATENT DOCUMENTS

| | | |
|---|---|---|
| JP | 2006-223703 A | 8/2006 |
| JP | 2008-061850 | 3/2008 |
| JP | 2008-086659 A | 4/2008 |
| JP | 2009-045432 A | 3/2009 |
| JP | 2009-080032 A | 4/2009 |
| WO | 2008/061850 | 8/2008 |

* cited by examiner

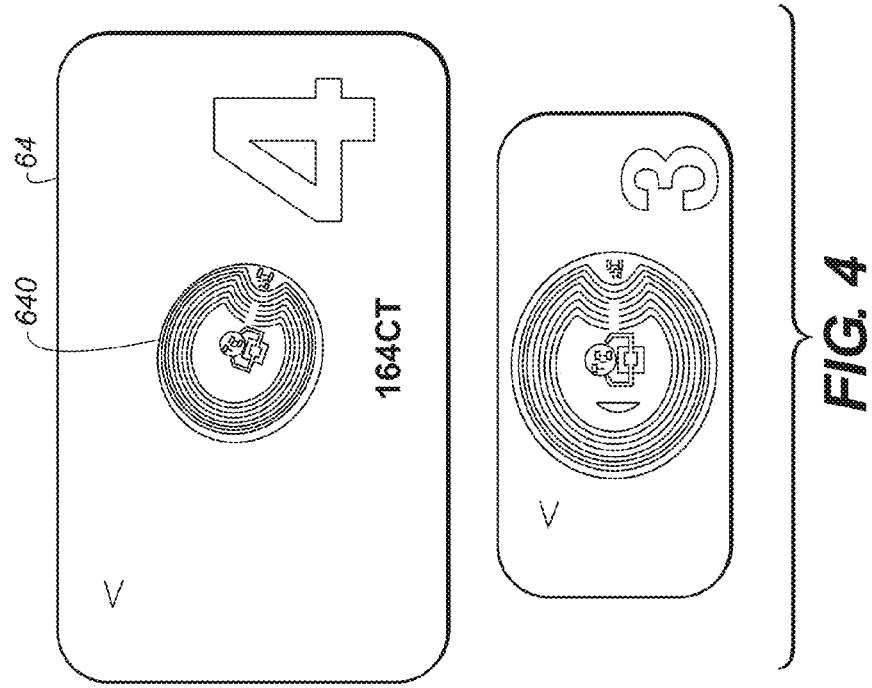
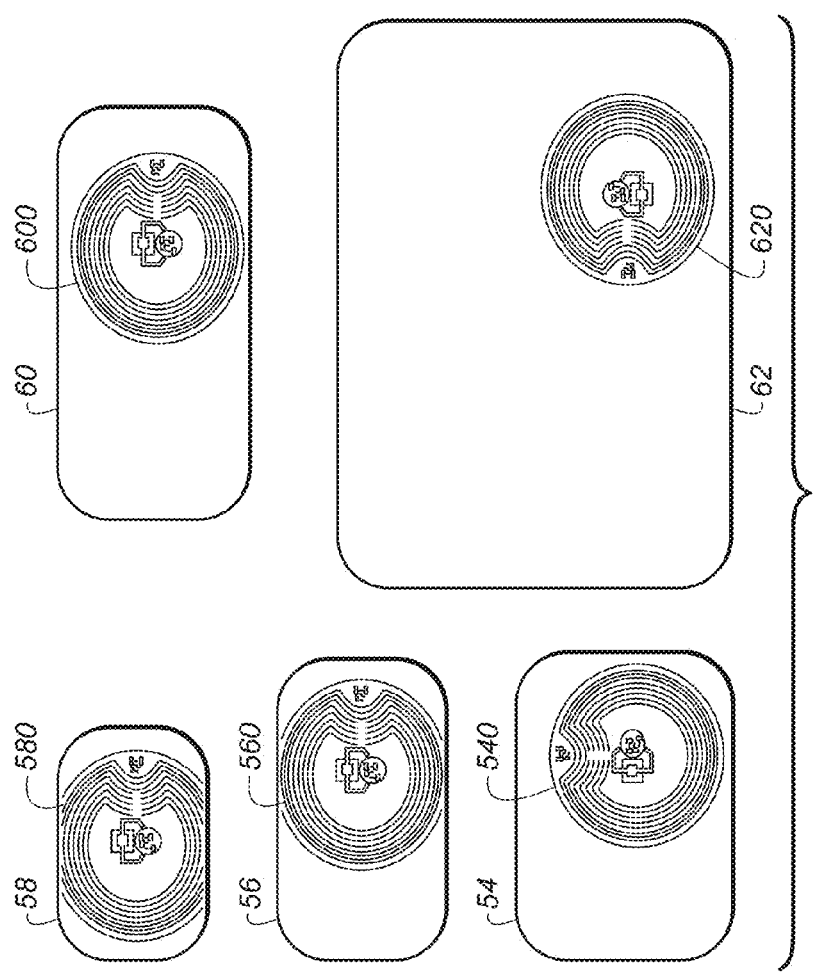

METHOD AND SYSTEM FOR COMPUTED RADIOGRAPHY USING A RADIO FREQUENCY IDENTIFICATION DEVICE

CROSS REFERENCE TO RELATED APPLICATIONS

This application is a Continuation of U.S. patent application Ser. No. 12/976,011, filed Dec. 22, 2010 in the names of Berger, entitled METHOD AND SYSTEM FOR COMPUTED RADIOGRAPHY, which itself claims priority to provisional U.S. Patent Application Ser. No. 61/334,331, filed May 13, 2010 in the names of Berger, entitled METHOD AND SYSTEM FOR COMPUTED RADIOGRAPHY, both of which are incorporated herein by reference.

FIELD OF THE INVENTION

The present invention relates to identification of medical items to prevent their intentional or inadvertent mismatch during use or reuse. More particularly, the present invention refers to identification, monitoring, and tracking of flexible information carrier plates used in computed radiography when the plates are circulating from exposure to X-rays to scanning. Even more particularly, the present invention refers to identification, monitoring, and tracking of flexible information carrier plates that are used in intra-oral dental imaging.

BACKGROUND OF THE INVENTION

The use of information carrier plates (also referred to as phosphor or phosphor storage plates) for obtaining visually perceptible contrast upon exposure to X-rays is known in the art as computed radiography (CR) and is described for example in U.S. Pat. No. 7,211,785 (Berger).

The imaging cycle employing such plates comprises juxtaposing the plate nearby a specific part of the body (e.g., leg, arm, tooth, and the like) and then exposing the plate to X-rays in order to obtain an image from stored radiation energy. Following exposure, the plate is then removed from the patient and the latent image that is stored thereon is scanned by a laser beam or other energy source to stimulate emission of the stored energy and to form corresponding image data from the emitted energy. After the plate has been scanned, the obtained image data can be displayed and stored for further examination. The exposed and scanned plate is then erased and can be reused in a subsequent imaging cycle.

It can be appreciated that each plate must be properly tracked throughout the imaging cycle as the plate circulates from X-ray exposure, to scanning, to erasure, and to re-use. That is, it must be possible, at each stage in this process, to know specific plate identification information as well as patient identification information and identification information concerning specific treatment with which a plate is associated.

This requirement is important for general medical computed radiography (CR) and becomes especially complex for intra-oral dental computed radiography applications. In dental clinics, large numbers of patients undergo X-ray examination, and therefore a large number of information carrier plates can be in circulation at any one time, thus increasing the probability for mismatch between a particular plate and the patient and treatment data associated with the plate, as well as with the obtained image on the plate. The probability for mismatch is especially high in a working environment where several treatment rooms, each equipped with an X-ray generator, share the same scanning device. Any mismatch can result in confusion, delay, waste, incorrect diagnosis, and the need to repeat an exposure in some cases. Other possible errors that can occur due to mismatch include inadvertent re-exposure of a plate that has not yet been erased.

The likelihood for error and the impact of an error can be further compounded when a full mouth scan is executed. This dramatically increases the number of plates used for a particular patient and requires careful tracking to avoid mistakes.

With intra-oral dental computed radiography, the mismatch between CR plates is not easily detectable to the eye, since different teeth can have a relatively similar appearance. The likelihood of confusion is high when compared with other medical radiography applications that image larger or more distinctive parts of the body about which there can be much less confusion.

Thus, positive and unequivocal identification, as well as monitoring and tracking of information carrier plates, is desired in computed radiography in general, and in intra-oral dental computed radiography in particular, since it helps to prevent patient mismatch and other errors.

There have been a number of attempts to address this problem.

One example can be found in U.S. Pat. No. 5,428,659 (Renner) disclosing digital memory configured as a PCB (printed circuit board).

In intra-oral dental computed radiography, the exposed information carrier plates are usually placed on a flat holder that is divided into cells referring to different teeth. A technician puts the CR carrier plates on the holder such that a certain plate occupies a certain cell. The pattern of the cells corresponds to the pattern of a template that is filled in by the dental practitioner before submitting the plates to X-ray exposure. The plates are moved from the treatment station to an X-ray station and then to a scanning station, lying on the holder in the order corresponding to the template pattern. In particular situations, this arrangement can be unreliable, for example, the plates can fall from the holder during handling. Their correct re-attribution to the corresponding cell can be complicated if the plates are not provided with some type of identification means.

Radio Frequency Identification Devices (RFID devices) are known for identification, tracking, and monitoring of various items. RFID tracking is used for identifying various items, like consumer goods, reusable and disposable items, people, animals and the like. This identification technology has been implemented in various technical and non-technical fields, including medicine.

An RFID system comprises two main components: (i) a transponder associated with an item to be identified, and (ii) an interrogator, separated from the transponder by a short distance, that comprises an antenna, a transceiver and a processing device. The interrogator component sends RF energy and an interrogating signal (if necessary) to the transponder and then receives an RF response signal from the transponder. The received signal is transferred to the processing device and is read.

The transponder, or so-called RFID tag, is affixed by a suitable method to the item to be identified and comprises an integrated circuit containing RF circuitry. This circuitry serves as memory for storing information to be transmitted as a signal to the processing device in the interrogator. The RFID tag also comprises an antenna for transmitting this signal. Reading the signal that has been sent by the transponder allows the item bearing the tag to be identified and monitored.

There have been attempts to implement this technology in computed radiography. Some examples are noted below.

U.S. Pat. No. 7,319,396 (Homanfar) and U.S. Pat. No. 7,518,518 (Homanfar) describe using an RFID tag.

U.S. Pat. No. 7,095,034 (Haug) describes image carriers enclosed in cassettes, with an RFID tag affixed to the edge region of the cassette.

U.S. Pat. No. 5,418,355 (Weil) describes storage media enclosed in a cassette wherein the media is provided with an identification bar code.

U.S. Pat. No. 4,739,480 (Oono) describes a label adhered to the image storage panel, with the panel stored in a cassette. The information carried by the label represents an identification code assigned to the panel.

U.S. Pat. No. 6,359,628, U.S. Pat. No. 5,757,021 (Dewaele) and EP Patent No. 0727696 (Dewaele) describe media contained in a rigid cassette with an RFID tag attached to a specific location on the cassette.

U.S. Pat. No. 4,960,994 (Muller) describes media that is used in association with a cassette and with a memory affixed to the cassette in a predetermined location.

U.S. Pat. No. 6,381,416 (Manico) describes use of an RFID tag in association with photographic film used in consumer photography, for example, for establishing conditions to be selected for processing of the film.

U.S. Pat. No. 8,374,461 (Humphreys) describes a digital radiography plate identification system.

U.S. Patent Application No. 2012/0019369 (Taskinen) describes an arrangement for controlling image plate and its image information and a method for controlling the arrangement.

U.S. Pat. No. 6,826,313 (Robar) describes a method and automated system for creating volumetric data sets.

U.S. Patent Application No. 2009/0212107 (Crucs) describes an auto-distribution of scanned digital images based on standardized identifiers.

U.S. Pat. No. 6,359,628 (Buytaert) describes combined identification and preview system for use in digital radiography.

U.S. Pat. No. 7,775,713 (Klemola) describes an arrangement for dental imaging.

While such solutions may employ RFID devices to help support the use of X-ray cassettes, however, there can be little or no improvement to the workflow process for dental imaging with these solutions. Persistent problems such as inconsistent labeling of plates, poor tracking of plate usage, and potential mismatch of images to patients continue to impede workflow efficiency in large dental practices.

Thus, despite attempts to employ RFID technology with various types of imaging media, there is room for improvement in providing an RFID solution tailored for specific workflow requirements of intra-oral dental computed radiography.

SUMMARY OF THE INVENTION

The present invention is intended to provide simple, convenient and reliable solution for identifying, monitoring and tracking flexible information carrier plates used in intra-oral dental computed radiography in order to prevent their inadvertent or intentional mismatch.

An object of the present invention is to provide a new method and system for dental radiography employing flexible information carrier plates, each provided with an RFID tag immediately affixed thereto, or using some other storage device that is accessible using wireless communication, to enable identification, monitoring, and tracking of the information carrier plates, whether the plates are enclosed in disposable or in re-usable envelopes.

Another object of the present invention is providing a new method and system for dental computed radiography employing RFID tags that can be attached to flexible information carrier plates, irrespective of plate size or specific location or side of the plate.

A further object of the present invention is providing a new method and system for dental computed radiography employing RFID tags, wherein memory can be loaded in wireless fashion with both permanent and temporary identification information.

Yet another object of the invention is providing a new method and system for computed dental radiography employing RFID tags in which memory can be loaded with identification information concerning the information carrier plate itself, as well as with identification information concerning a dental treatment to be carried out.

Another object of the invention is providing a new method and system for computed dental radiography in which the identification information concerning dental treatment comprises at least data associated with a patient and with specific conditions for examination.

Still another object of the invention is providing a new method and system for dental computed radiography in which the identification information concerning the information carrier plate comprises e.g., plate size and type, manufacturing date, first scan date (activation date), scan count, job number, resolution, destination address and scan status.

Still another object of the invention is providing a flexible, information carrier plate for intra-oral computed radiography, the plate being substantially flat and defined by two opposite sides, the plate bearing a RFID transponder affixed immediate to one of its opposite sides, the transponder comprising a memory for storing information therein.

According to one embodiment, the present invention provides a method for obtaining an intra-oral X-ray image of a subject on a flexible information carrier plate for computed radiography, the method comprising: affixing a memory to a surface of the information carrier plate, wherein the affixed memory stores information about the plate and wherein the affixed memory is in wireless communication with a computer; storing at least a first scan date in the affixed memory; obtaining the intra-oral X-ray image of the subject using steps of: (i) storing at least a job identifier and a scan status for the plate in the affixed memory; (ii) acquiring image data from a scan of the flexible information carrier plate following exposure to X-rays, acquiring at least the job identifier from the affixed memory, and associating the acquired image data with the acquired job identifier; (iii) incrementing a scan count value and updating the scan status in the affixed memory of the exposed flexible information carrier plate; (iv) erasing image content from the flexible information carrier plate; and (v) storing the acquired image data in a second, computer-accessible memory according to the acquired job identifier.

For a better understanding of the present invention as well of its benefits and advantages, reference will now be made to the following description of various exemplary embodiments taken in combination with the accompanying drawings.

BRIEF DESCRIPTION OF THE DRAWINGS

FIGS. 3 and 4 show examples of flexible carrier plates provided with RFID tags in accordance with the present invention.

DETAILED DESCRIPTION OF THE INVENTION

It is noted that the present invention is not limited to medical radiography in general or to intra-oral dental radiography in particular. The present invention is suitable for other medical and non-medical applications as well.

In the context of the present disclosure, the equivalent terms "flexible information carrier plate", "flexible plate", "CR plate" or simply "plate" refer to photo-stimulable phosphor plates (PSP plates) that are used for image storage in the computed radiography CR arts, deployed in a manner analogous to the photographic plates that they have replaced in many applications. The information carrier plate is considered flexible when it has at least some degree of conformance to curvatures useful for intra-oral imaging.

In the context of the present disclosure, the term "scanner" or "scanning device" refers to a device or apparatus that is capable of obtaining stored image data from the flexible information carrier plate following exposure of the plate. The scanner typically stimulates the phosphor storage media using a laser beam. As the beam energy passes over the plate surface, it frees electrons "trapped" in "color centers" in the crystal lattice of the X-rayed phosphor plate. The light emitted during laser stimulation can be collected and the resulting signal converted into a digital image by a computer or other dedicated logic processor. The location at which the scanner is deployed is referred to as a scanning station.

Figure 1:
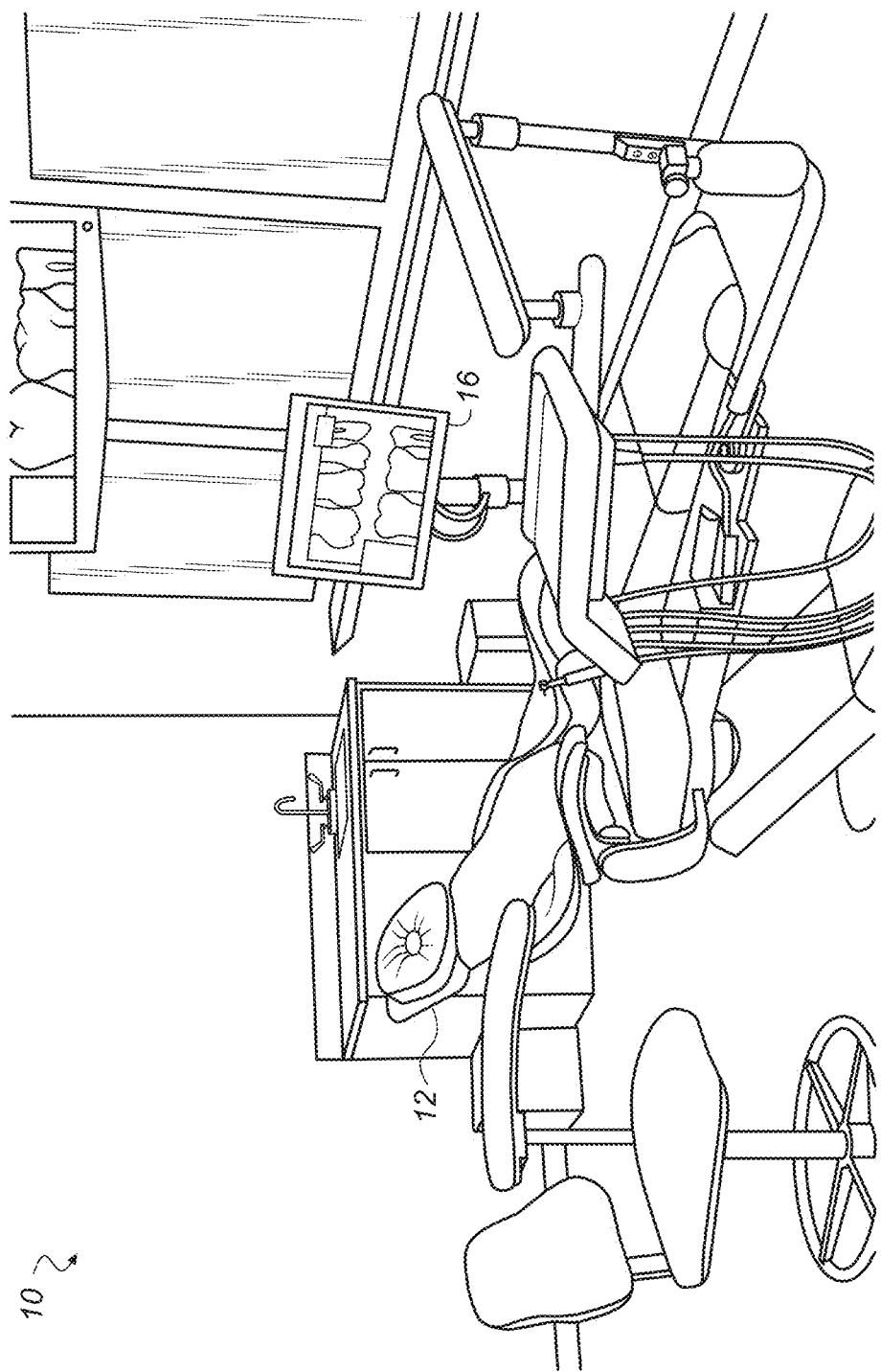
FIG. 1 shows a general treatment room used by a practitioner and provided with a chair working station.

Referring now to FIG. 1, there is shown a typical dental treatment room 10 of a practitioner. The treatment room inter alia comprises a treatment chair 12 having a console with various instruments as required for dental treatment, e.g. intra-oral treatment.

The treatment room is preferably equipped with a suitable interface terminal that serves as a processing and acquisition station for input, output, and management of data and possibly including a keyboard with mouse. It is not shown specifically but should be appreciated that the interface communicates over a network, for example, via a local Ethernet network, with a suitable server providing access to a database and a software application enabling management of medical and personal data related to a medical case. The application also allows acquisition, viewing, and processing of images obtained after scanning, archiving the images and related data, and other functions. In an alternate embodiment, such as in a small clinic, the interface may communicate with a local computer workstation or personal computer (PC), instead of with a networked server.

The treatment room is suitable for computed intra-oral dental radiography and is equipped with a monitor 16, e.g., a LCD (Liquid Crystal Display) for displaying images acquired after X-ray exposure and scanning. It is not shown in FIG. 1 but should be appreciated that a plurality of flexible information carrier plates are available, typically stored in the vicinity of the treatment chair.

While not shown in FIG. 1, it would be appreciated that the treatment room can also comprise an X-ray generator, which may be situated either in the treatment room itself or adjacent thereto. In a small treatment room, a scanner can also be provided for obtaining the stored image data obtained after exposing the information carrier plates to X-rays. However location within the treatment room is not compulsory, since the practitioner can alternately use a scanner that is situated apart from the treatment room.

In the present disclosure, the treatment room is alternately referred to as a working station. If the working station is equipped with a scanner dedicated solely to this station, then the possibility for mismatch of the plates is less likely. This possibility, however, still exists and therefore it would be desirable to render the plates identifiable in some way even for such a basic system.

Figure 2:
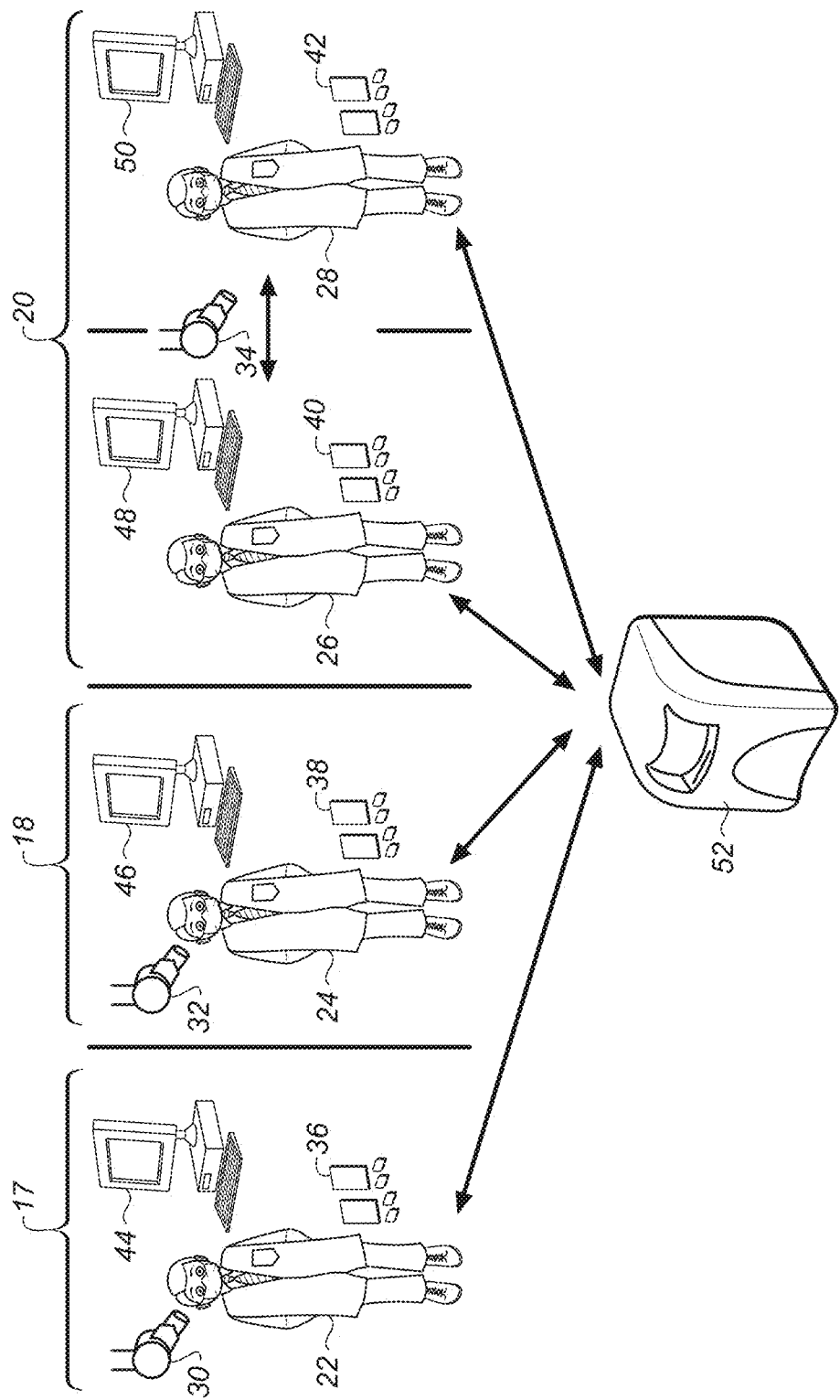
FIG. 2 depicts examples of working environment in which several practitioners occupy separate working stations and share the same scanning station.

FIG. 2 shows a schematic of another exemplary working environment for intra-oral computed radiography. This environment is more prone to mismatch than the single working station of FIG. 1 and therefore requires more careful identification of the information carrier plates. This working environment comprises a plurality, for example three, separate working stations 17, 18, 20. Working stations 17 and 18 are used by two respective practitioners 22 and 24. Working station 20 is used by two neighboring practitioners 26 and 28. Each working station is equipped with a respective X-ray generator 30, 32, 34. The generator 34 is shared by practitioners 26 and 28.

Each practitioner has sufficient stock 36, 38, 40, 42 of flexible information carrier plates, here designated as media. Each working station has a computer with respective LCD monitor 44, 46, 48, 50 and respective keyboard and mouse.

It is also seen in FIG. 2 that all working stations communicate with a common scanner 52 installed in a separate room, e.g., a disinfection room or a surgery room. This scanner is shared by all practitioners and therefore, in order to organize the workflow efficiently, the scanning step should be synchronized with the X-ray exposure step so that each practitioner reserves the scanner for plate processing before sending the exposed plates to scanning.

In an environment such as that shown in FIG. 2, a substantial number of exposed plates requiring scanning can be generated (especially where full mouth imaging is needed for one or more patients). The likelihood of mismatch is high. In the event of such a mismatch, the scanning step constitutes a bottleneck to the whole workflow. Therefore, in a working environment of this type wherein a single scanner is shared by several working stations, it is especially important to prevent mismatch between plates as they circulate between many working stations and scanner.

In accordance with the invention, the mismatch can be prevented by providing the plates with identification means rendering them immediately attributable. It would then be possible to improve the workflow and to proceed through the treatment plan more efficiently without disrupting daily operation.

In accordance with the present invention, the information carrier plates are provided with an affixed RFID transponder or tag that has a memory that can be loaded with both permanent and temporary information. The RFID tag enables memory on the information carrier plate to be in communication with a computer. Also provided is an RFID interrogator or tagging device. Here by tagging device is meant any read/write device that is capable of reading data stored in the memory of the RFID tag as well as capable of loading the RFID tag's memory with permanent and/or temporary data and/or updating the temporary information stored in the memory. The tagging device is provided either only at the scanner or at both the scanner and the working station and can be, but is not necessarily, located near the corresponding scanner or working station, but may be separated from other equipment, such as using wireless communication. Regardless of its location, the tagging device communicates with the data management software and is automatically detected by the software. The tag's affixed memory can be loaded with the information and the stored information can be read using the tagging device.

FIGS. 3 and 4 show a few examples of flexible intra-oral dental plates provided with RFID identification means in accordance with the present invention. FIG. 3 shows carrier plates 54, 56, 58, 60, 62 of different sizes. The plates are shown without disposable sachets or envelopes in which plates are normally enclosed when the practitioner places them in the patient's mouth for exposure to X-rays. Each plate bears a respective integrated circuit 540, 560, 580, 600, 620 constituting an RFID tag. The RFID tag is disposed immediately on the plate's surface and can be secured thereon by adhesive, for example. In FIG. 3, the tags are secured immediately on a rear side of the plates. The tags can be affixed to different locations of the plates depending on the plate's size. In FIG. 4, a plate 64 has an RFID tag 640 affixed immediately to a frontal side of the plate such that information about manufacturer and plate's size is also visible. FIG. 4 shows an embodiment with an RFID tag affixed to a frontal side of a plate of smaller size. It can be appreciated that, in accordance with embodiments of the present invention, the RFID tag could be affixed immediately to the rear side of a plate.

A suitable RFID tag can include a type of commercially available RFID transponder, e.g., HF 15×15 mm Dry Inlay, sales code 3001059, manufactured by UPM Raflatec, Finland. Other commercially available transponders can be used as well. A suitable interrogator can similarly be a commercially available product, e.g. HNI002 HF, manufactured by ClarIDy Solutions, Inc., Taiwan.

Figure 5A:
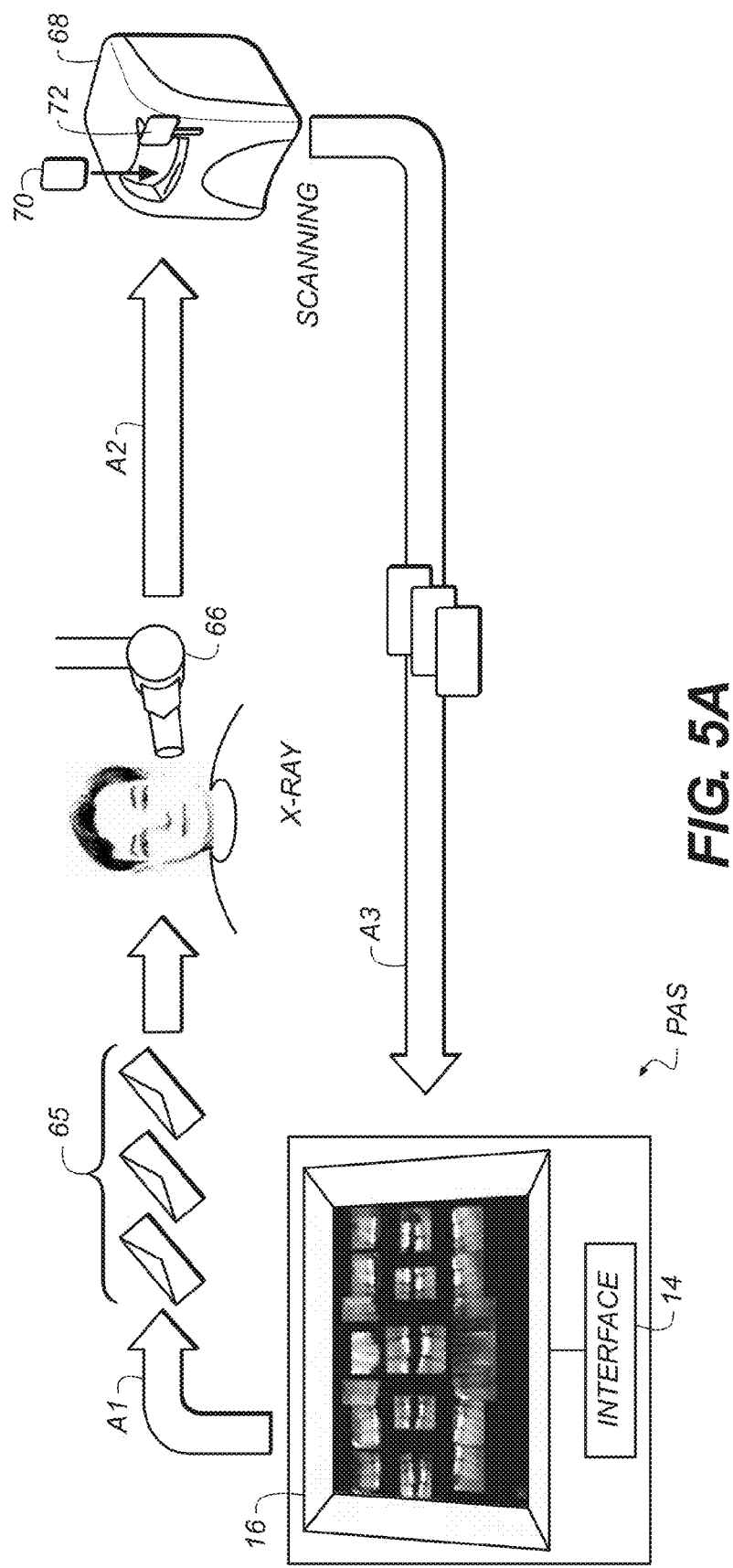
FIG. 5A shows a working cycle in which tagging of carrier plates is carried out at the scanning station.

In FIG. 5A is depicted an example of a working cycle suitable for information carrier plates with affixed RFID tags in accordance with an embodiment of the present invention. A processing and acquisition station (PAS) has an interface 14 coupled with monitor 16 on which are displayed images acquired during previous scanning. It is seen also that a plurality of intra-oral information carrier plates 65, enclosed in disposable envelopes, proceed as shown by arrow A1, from the processing and acquisition station to X-ray generator 66. The plates intended for exposure are not yet imaged, with any previously obtained image erased from their surface after scanning. Each plate is provided with an RFID tag that has its memory loaded with permanent information referring to manufacturing data and plate size. The memory is also loaded with temporary information that can be updated by the tagging device in the course of the working cycle. Among temporary information writable in the memory of the affixed RFID tag is data such as first scan date, scan count and scan status. Scan status can include information such as Scanned and Erased or Tagged and Ready for Exposure, for example.

The plates are put in the mouth of a patient nearby the teeth to be examined. Upon completing X-ray exposure, the plates pass, as shown by an arrow A2, to the scanning station for scanning in a scanner 68. Before scanning the envelopes are removed from the plates. One such plate is designated by numeral 70; the plate itself may also include other useful information, such as a size or number indicative of size, for example. The plate is ready for insertion into the entry slot of the scanner. A tagging device 72 is deployed at the scanner, preferably housed within the scanner, and is in communication with the computer or processing and acquisition station. Tagging device 72 enables communication of the RFID tags with the computer or host workstation that is associated with the treatment room.

The tagging device has an antenna communicating with the respective antenna of the RFID tag affixed to the plate, so that information stored in the tag's memory is readable and can be available to the practitioner on the monitor of the working station or, if the scanner has a dedicated display, at the scanner itself. When the plate passes scanning the first time, the tagging device writes the first scan date in the memory of the RFID tag. Upon each subsequent scanning operation, the tagging device sends a signal that is received by the antenna of the RFID tag and that increments the scan count stored in the tag's memory. This signal also updates the scan status of the plate, i.e. whether the plate has already been scanned or not. This feature makes it possible to more easily monitor the service life of the plate and its scan status. For example, the scan count can be compared against a threshold count value and the result reported when a plate exceeds the threshold. Optionally, the tagging device can be set up to disable use of a plate having a scan count above a threshold value.

When scanning is completed, the scan count is updated in the tag's memory and the obtained image is sent by the scanner to the processing and acquisition station (PAS). If the scanner is provided with a display, the image can be viewed on that display as well. Then, the plate is erased and proceeds back to the processing and acquisition station. FIG. 5A shows schematically a plurality of erased plates proceeding back to the processing and acquisition station as indicated by an arrow A3. At the working station, the erased plates are put into disposable envelopes and are ready for the next working cycle.

The above working cycle is especially suitable for small clinics, in which the available scanner is not shared by several practitioners.

Figure 5B:
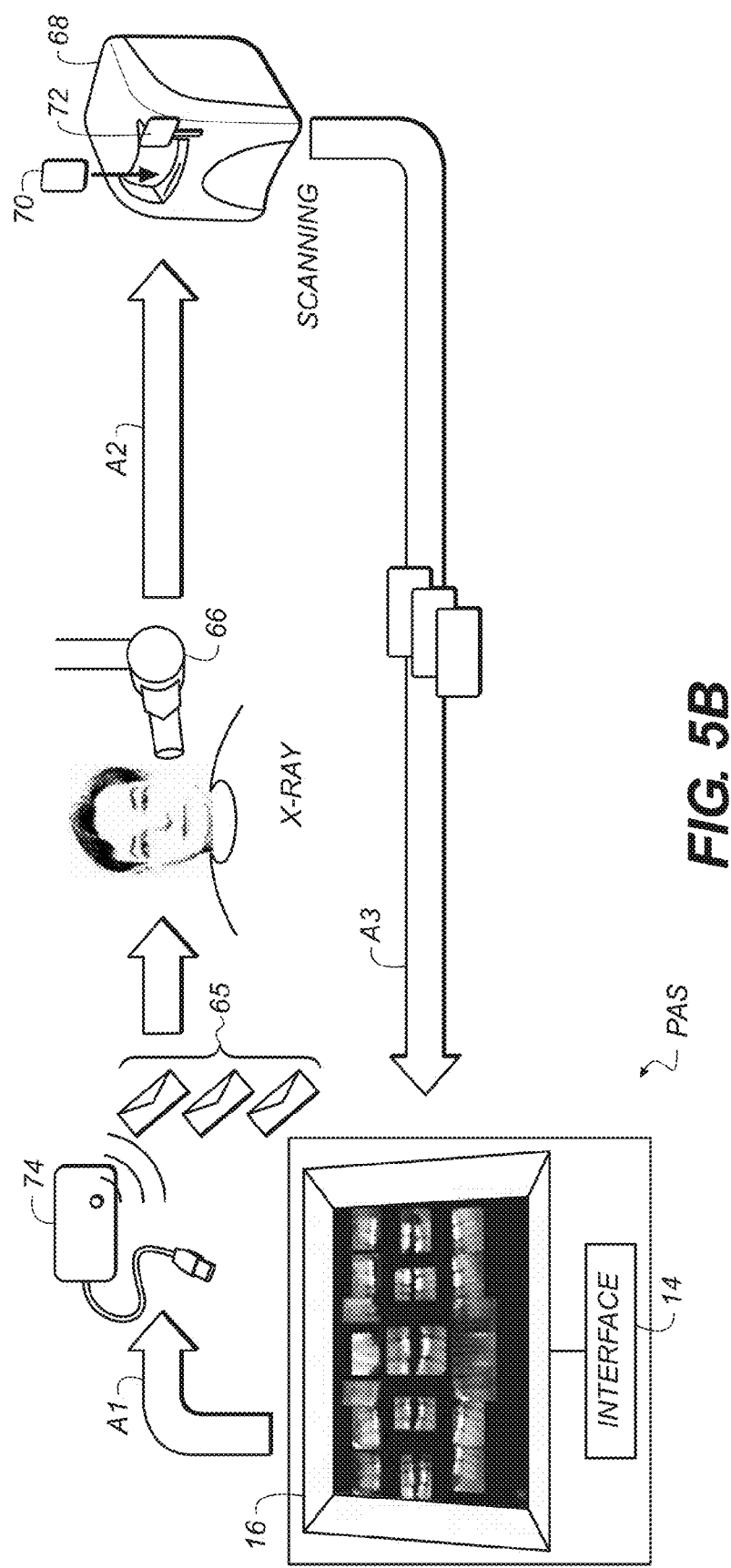
FIG. 5B shows a working cycle in which tagging of carrier plates is carried out at the working station and at the scanning station.

In FIG. 5B, there is shown another example of a working cycle in accordance with the present invention. This working cycle is suitable for the situation in which several practitioners share the same scanning station. In general, this working cycle is rather similar to the previous one and therefore similar elements are designated by the same reference numerals. However in contrast to the working cycle embodiment shown in FIG. 5A, the FIG. 5B embodiment provides an additional tagging device, namely secondary RFID interrogator 74. This tagging device is intended for tagging a plurality of erased image carrier plates 65 before they are put in the patient's mouth at the X-ray station. As a suitable secondary RFID interrogator one can use, for example, an Explore-R RFID reader, type HFE-00-003 manufactured by Tracient Technologies Ltd., New Zealand.

The plates are tagged while enclosed in envelopes. The tagging device, interrogator 74, communicates with the processing and acquisition station (PAS) by a suitable wired or wireless connection.

It is noted that tagging devices and interrogator devices are associated with and in communication with scanner and processing and acquisition station devices, but may be positioned at some other location rather than at these devices themselves, such as at a location that is more favorable for the workflow. In one embodiment, wireless communication between tagging and interrogator devices and their corresponding processing and acquisition station or scanner devices allows considerable flexibility for device placement.

During this working cycle, updating of information in the memory of the RFID tag takes place before scanning at the processing and acquisition station and then at the scanning station.

During the tagging step, which takes place at the processing and acquisition station (PAS), the tagging device writes temporary information into the memory of the RFID tag. The temporary information comprises inter alia, job number or other type of job identifier that relates to a particular imaging session or "job", resolution, destination address. Furthermore the temporary information comprises patient identification data that is up-loaded from the data base system, to which the processing and acquisition station has access. The patient identification data is also accessible in the data base at the processing and acquisition station. This data refers to job number or other type of job identifier, a random number written in the memory of the RFID tag. When scanning is completed and the image is sent from the scanner to the processing and acquisition station, it is displayed on monitor 16.

Now with reference to FIG. 6 an embodiment of a system for intra-oral computed radiography in accordance with the present invention will be explained. In this embodiment the system comprises the following basic elements:

a) a plurality of working stations 75, 76, 78 each of which is equipped with a treatment chair and X-ray generator and each having a respective processing and acquisition station 80, 82, 84 with access to appropriate application software;

b) a plurality of scanning devices 86, 88, 90 provided with respective tagging devices 860, 880, 900;

c) a plurality of flexible information carrier plates 92 having respective RFID tags affixed immediate to one of their sides;

d) a plurality of tagging devices 800, 820, 840 associated with and in communication with respective working stations PAS 80, 82, 84 and operable for tagging information carrier plates before the plates are exposed to X-rays; and e) a server 94 providing access to a database 940 and appropriate data management system.

Figure 6:
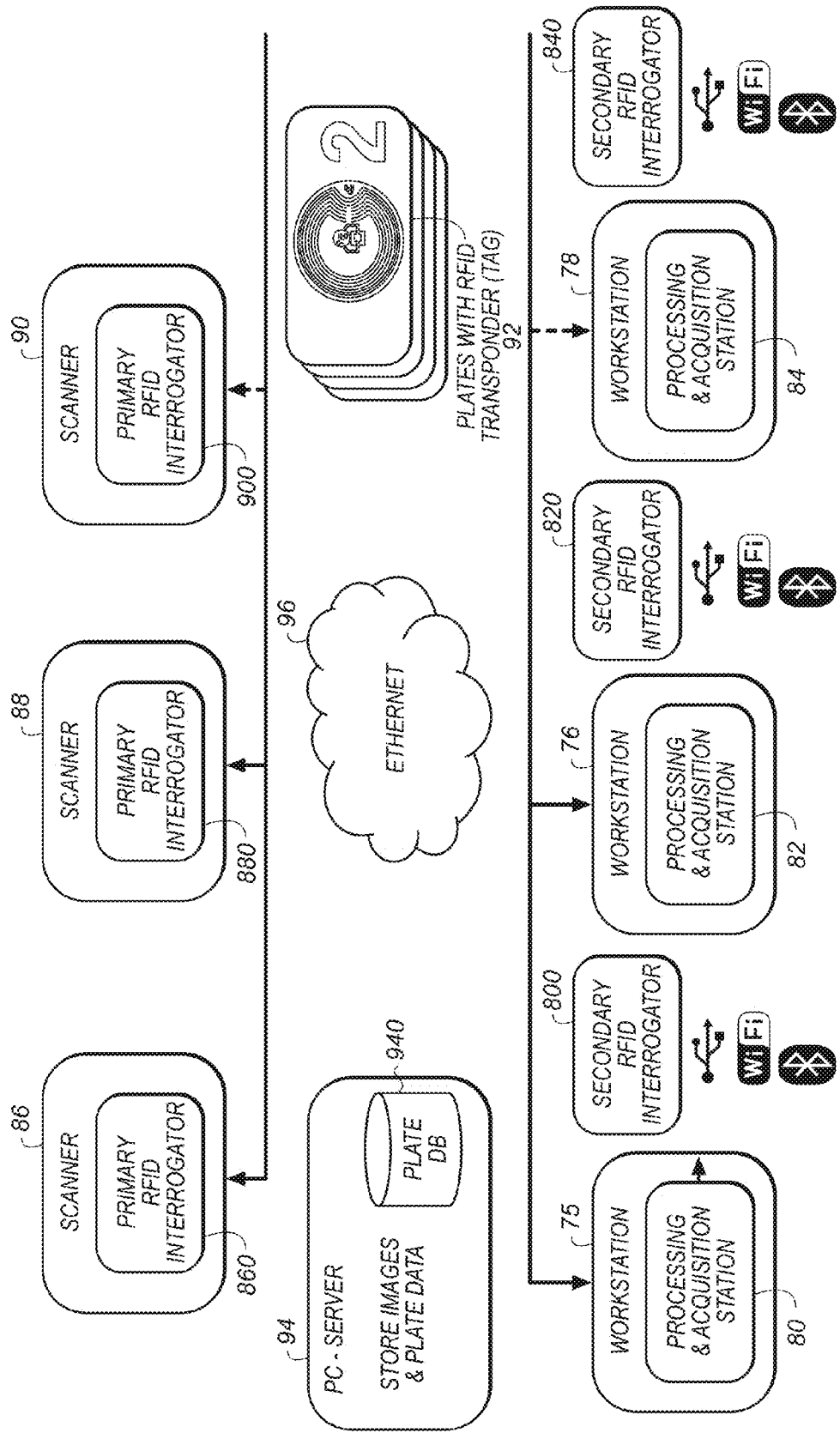
FIG. 6 depicts schematically a system for intra-oral computed radiography in accordance with the present invention.

As is shown in FIG. 6, working stations, scanners, and server can communicate between each other via connection over an appropriate network, e.g., Ethernet network 96. With network connection, messages can readily be sent from the scanner to the processing and acquisition station and vice versa, as well as files with scanned images for storing the database.

In the system of FIG. 6, tagging devices 800, 820, 840 that refer to working stations 75, 76, and 78 can communicate with respective processing and acquisition stations 80, 82, 84. In one embodiment, this communication uses a USB connection. Wireless communication is available in an alternate embodiment, through WiFi (Institute of Electrical and Electronics Engineers (IEEE) 802.11 standard, generally termed WiFi) or Bluetooth connection. One should appreciate that these devices can communicate as well through any other suitable wire or wireless connection that enables exchange of data.

It is noted that the system of the present invention may have more or fewer than three working stations and three scanners as depicted in FIG. 6. For example, one can contemplate a system comprising a single working station and one scanner, or one working station and several scanners, or several working stations and one scanner. The number of working stations need not be equal to the number of scanners and vice versa. One should also bear in mind that in a configuration when the system consists of single working station and single scanner, the tagging device at the working station can be absent and such a system can function in accordance with the working cycle explained in connection with FIG. 5A. This is irrespective of the sequence in which the plates have been tagged. It is appreciated that this is advantageous since it saves practitioner time required for matching between an individual plate and the template window associated with the plate. The template and its windows are explained in more detail subsequently.

In such a system, the server and networked communication via the Ethernet are not necessary; instead, the working station itself can be equipped with a PC loaded with database, data management system, and processing and acquisition software.

It is noted that tagging devices that are provided at working stations and at scanners, that is, are in communication with computer and other equipment at working stations and with scanners, are operable to both read and write or amend information stored in the memory of RFID tags in order to update it as part of the tagging operation.

Figure 7:
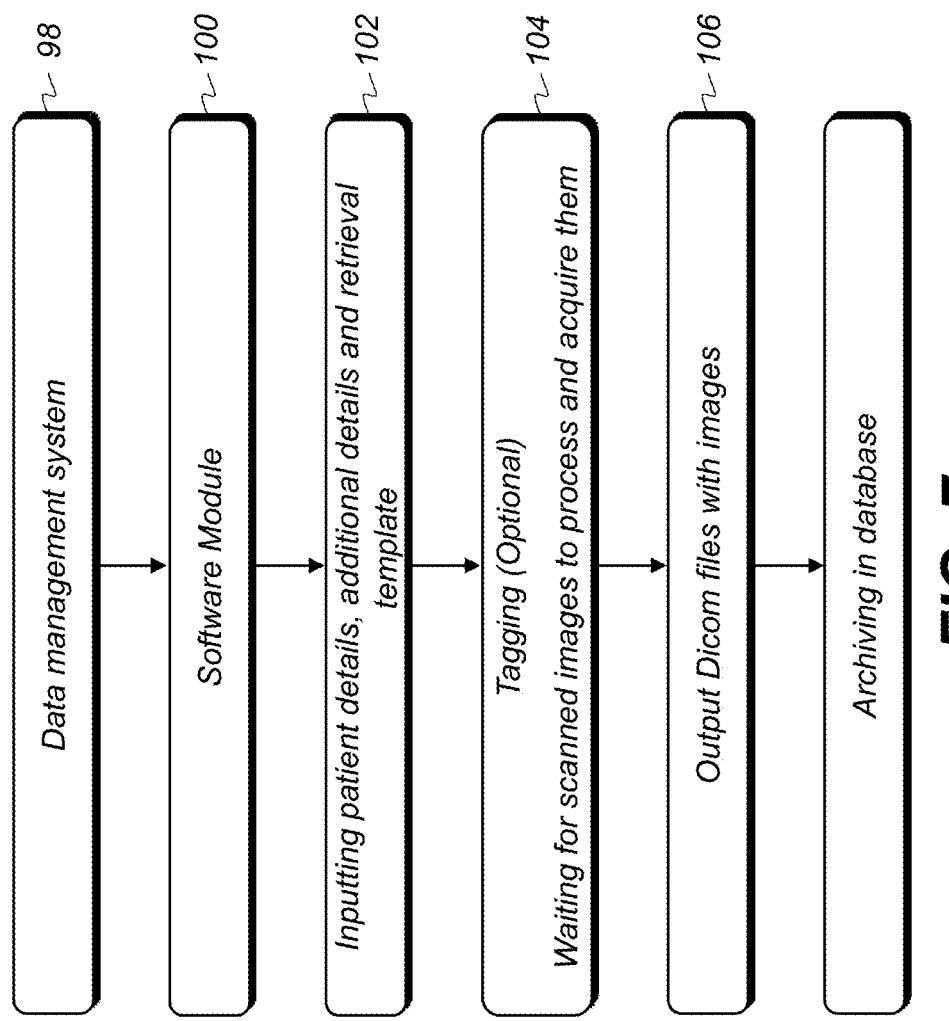
FIG. 7 is a block diagram of the input, acquisition, and output of data circulating in the system shown in FIG. 6.

FIG. 7 shows a block diagram of the data flow taking place in the system of the present invention. The flow of data comprises input, processing and acquisition, and output of data. This flow is enabled and controlled by data management system software 98, e.g. a department patient management system. The management system is provided with a database for archiving data and with appropriate software module 100 for acquisition of images and data. One example of suitable software is KDIS (Kodak Dental Imaging Software).

The input step is designated by reference numeral 102. The data inputted by the software module is downloaded from the database. This data comprises patient details, previous treatment detail, and previously stored images. The input step 102 also comprises retrieval of appropriate templates that should be completed prior to treatment.

The processing and acquisition of data is designated by reference numeral 104. This step is associated with the scanner, when scanned image is sent from scanner to working station. This step is also associated with tagging when the tagging device (at the scanner and/or at the working station) writes information in the memory of the RFID tag and communicates with the data management system to report about various events which have taken place or should take place. If the system is provided with a tagging device at the scanner and there is no tagging device at the working station, the reported event, inter alia, is "scanning is completed". If the tagging device is provided at the working station then the reported event is, inter alia, the necessity of assigning new job number or other type of job identifier, which should refer to the data downloaded from the database. The job number is an assigned number, such as a random number that can be generated by the data managing system itself or can be taken from the stock of previously generated and stored random numbers.

The output of data is designated by reference numeral 106. This step takes place upon completing the scanning and comprises acquisition of the image and sending it to the database for archiving. The acquired image is archived preferably as DICOM file (Digital Imaging and Communications in Medicine Format Bitmap file).

Figure 8:
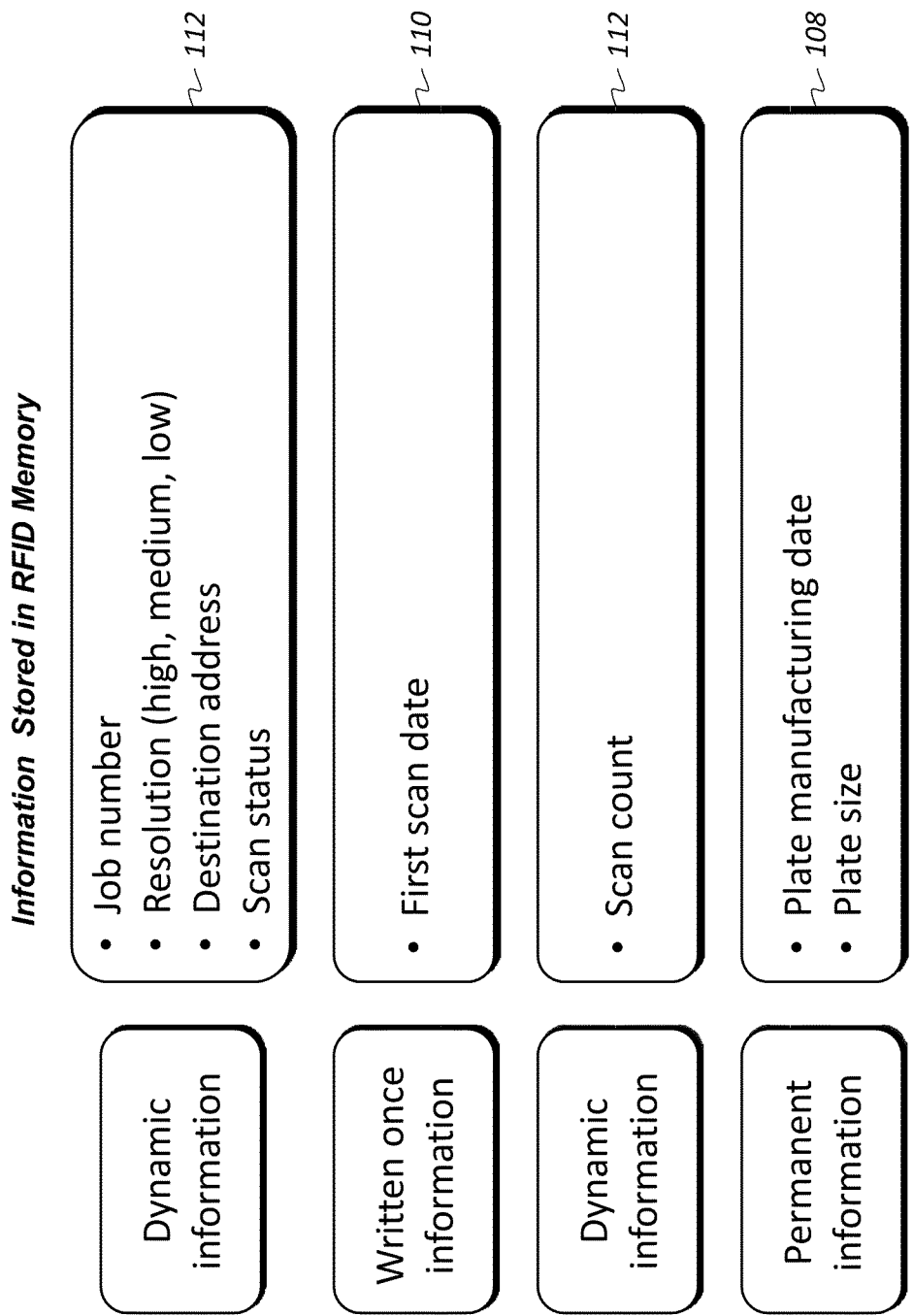
FIG. 8 depicts schematically the structure of information stored in the memory of an RFID tag attached to flexible carrier plates shown in FIGS. 3 and 4.

In FIG. 8, there is shown the structure of information that is stored in the memory of the RFID tag according to one embodiment. As previously stated, this information consists of permanent data, which is written once and is not amended during the working cycle, and of temporary data, which can be amended during the working cycle by tagging. This data will be referred to further as dynamic data.

The permanent data comprises data written by manufacturer of the plate and data written by the tagging device. The dynamic data is always written by the tagging device.

So, for example, the permanent data written by the manufacturer comprises data 108 referring to manufacturing date, plate size and type. The memory allocated to data 108 comprises two blocks of 32 bits each in one embodiment.

Permanent data which is written once by the tagging device at the scanning station comprises data 110, which stores the activation date (first scan date). Size and other characteristics of the plate can also be stored in the permanent data. The memory allocated for this comprises one block of 32 bits in one embodiment.

Dynamic data is designated by reference numeral 112 and may comprise, for example, the following types of data: job number or other type of job identifier, required resolution of scanning (high, medium, low), destination address (to which working station to send the scanned image for acquisition), scan status (whether or not the plate has already been scanned) and scan count (number of scans the plate has undergone). The memory allocated for dynamic data comprises five blocks of 32 bits each in one embodiment.

Depending on type, the dynamic data can be amended either by the tagging device available at the working station, or by a tagging device available at the scanner. So, for example, scan count and scan status is amendable by the tagging device at the scanner, while job number or identifier, resolution and destination address are amendable by the tagging device at the working station.

The dynamic data written by the tagging device is recognizable by the software application available at the processing and acquisition station, such that patient identification data extracted from the database during the input step is always linked with the job number or other type of job identifier that is written in the memory of the RFID tag.

Figure 9:
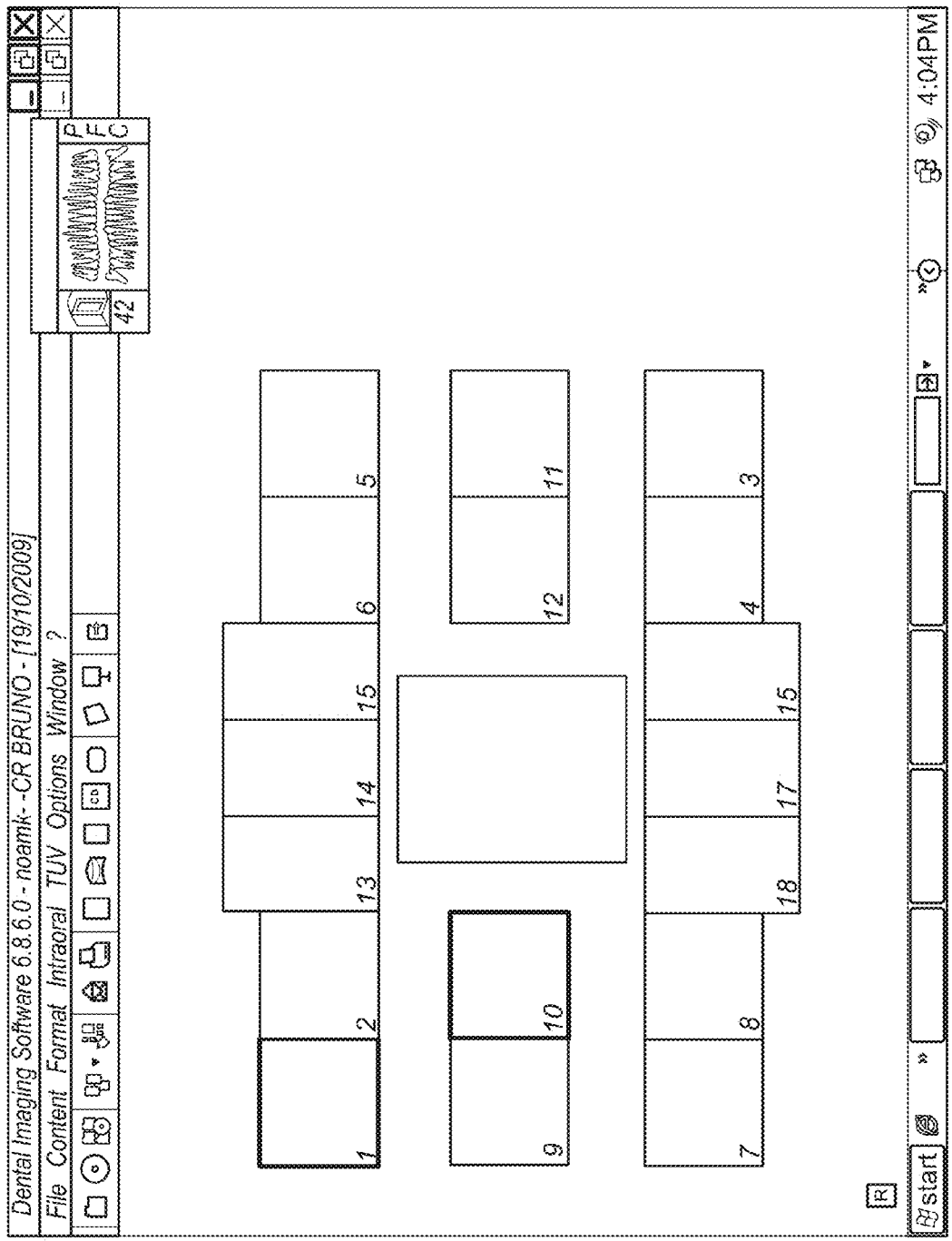
FIG. 9 shows an example of a GUI template used by a practitioner before acquisition of images from a scanning station.

The patient identification data is displayed in the electronic template at the beginning of the working cycle. In FIG. 9, there is shown an example of a suitable GUI template that can be associated with a study folder in one embodiment. Other GUI templates can be used as well. The electronic template automatically opens during the input step and consists of empty windows arranged in a pattern compatible with the normal arrangement of human teeth. When the template opens, it displays patient identification details, date of treatment, and the like. During the input step, the practitioner can select, e.g. by clicking with mouse, those windows that refer to teeth to be treated, and then highlights the selected windows. In the electronic template shown in FIG. 9, two windows are seen as being highlighted during the input step. The highlighted windows refer to particular teeth that should be examined. If the working station is equipped with the tagging device, then selection of windows can be synchronized with the tagging such that during tagging, a particular information carrier plate is assigned to a particular tooth of a particular patient.

Furthermore, during the tagging process, a job number or other type of job identifier is also generated. The job number is written in the memory of the RFID tag by the tagging device and is stored by the software application in association with the extracted patient identification data. Thus, a particular job number or other identifier constitutes a link between a certain plate and between details of treatment of a particular tooth of a particular patient. With this arrangement, it would be possible to positively identify the plate and attribute it to a particular patient and to a particular treatment. Eventually, all required windows in the electronic template GUI of FIG. 9 are highlighted by the practitioner in accordance with the treatment plan and linked by the job number with respective carrier plates.

For certain treatment plans, e.g., full mouth shot, selection of windows during the tagging process might take place automatically without clicking a mouse or using some other selection device. That is, a fixed sequence may be followed for assigning each plate in the series.

Figure 10:
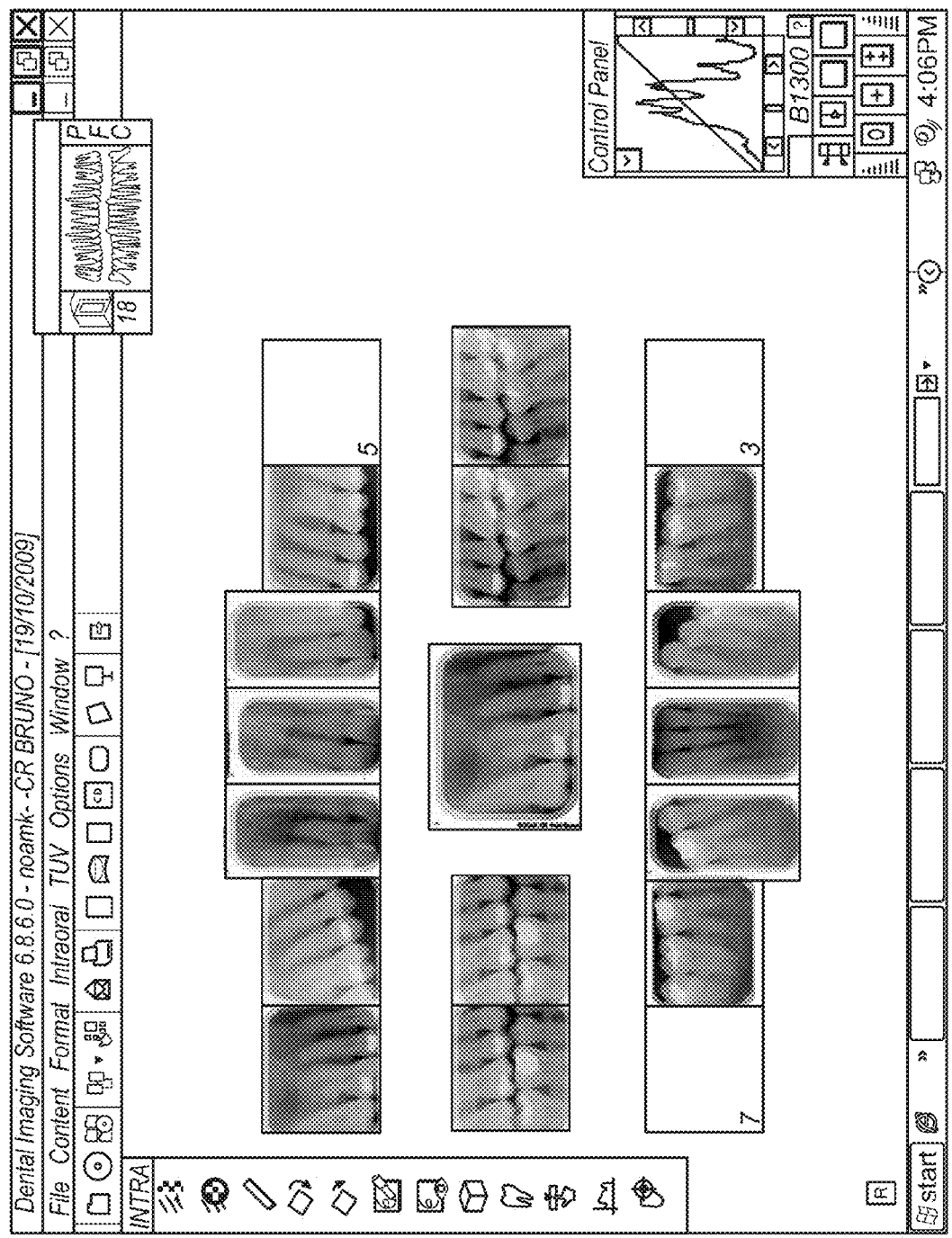
FIG. 10 shows an example of a GUI template after acquisition of images from a scanning station.

Upon completing the input step the tagged carrier plates pass to subsequent processes: exposure to X-rays followed by scanning. The obtained images are sent by the scanner to the working station where they are displayed on the monitor in the windows corresponding to assigned plates. An example of such a template displaying the acquired images in respective windows is seen in FIG. 10. In one embodiment, the displayed template corresponds to the study folder that is set up for patient images, as described previously, so that there is a 1:1 correspondence between template images and study folder images.

Figure 11:
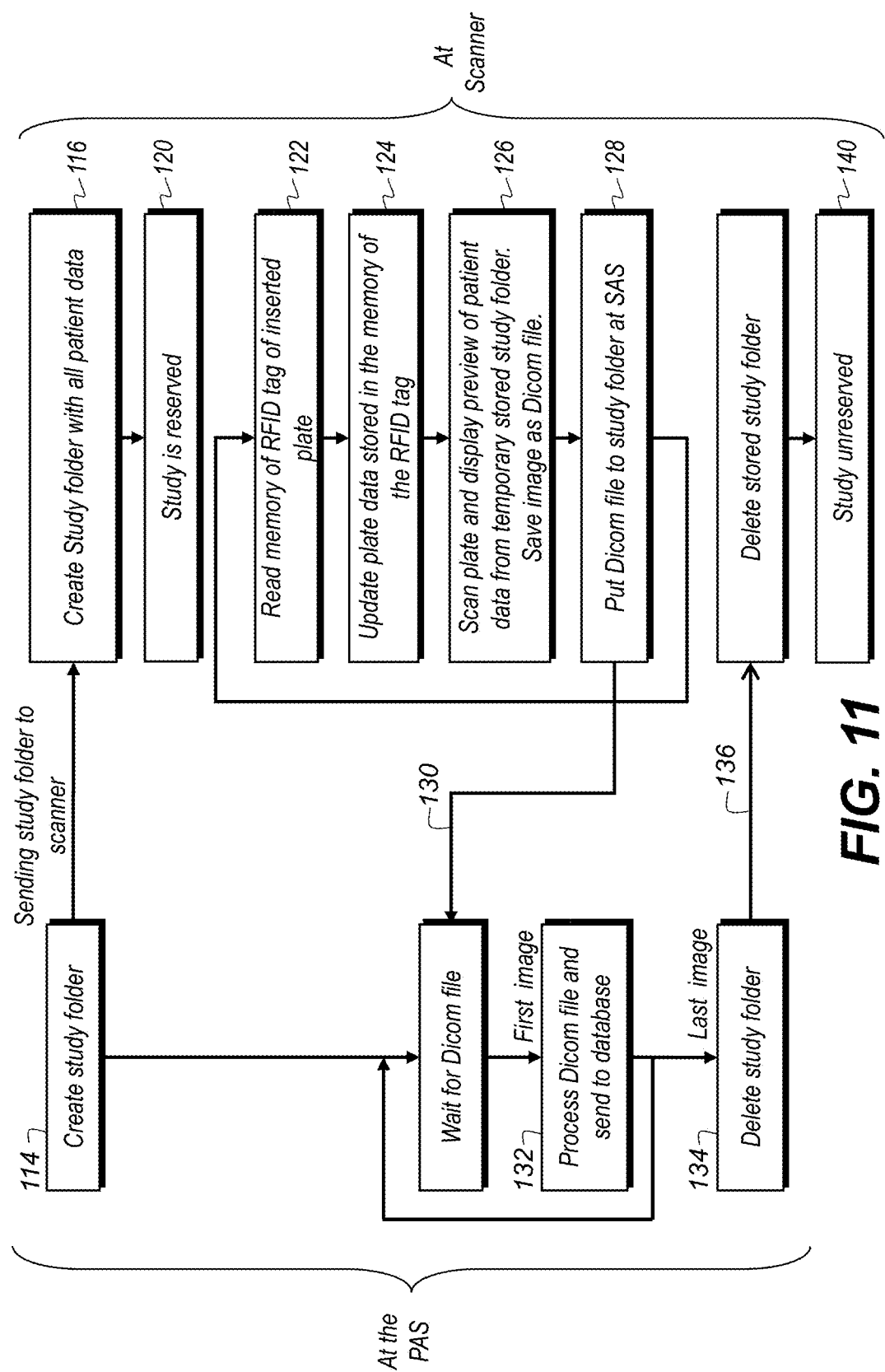
FIG. 11 is a block diagram of the working cycle shown in FIG. 5A.

The block diagram of FIG. 11 shows the interaction that takes place between the processing and acquisition station and the scanning station during computed intra-oral radiography in embodiments of the present invention. In the sequence of FIG. 11, only a single tagging device is deployed at the scanning station. In this situation, information carrier plates are provided with RFID tags with memory storing permanent data 108 (manufacturing date and plate size) as well as written-once data 110 (first scan date) and dynamic data 112 (scan count and scan status). The other types of dynamic data (job number, resolution, destination address) are not written, although memory blocks are allocated for this dynamic data to be written when necessary.

In the beginning of the working cycle, the processing and acquisition application software prepares the working cycle. This creates a study folder with patient identification information (patient data) and other treatment study data available from the database. This process step is designated by reference numeral 114. The study folder along with the treatment details (job details), e.g. tooth number, scan resolution and the like is also sent to the scanner which receives it and temporarily stores it as designated by a step 116. The software also displays, on the working station screen, a template with the study data and with windows assigned to certain teeth to be treated, as has been already explained above with reference to FIG. 9.

Continuing with the sequence of FIG. 11, erased image carrier plates that were assigned to the selected windows now proceed to X-ray exposure. The plates are typically enclosed in disposable envelopes; however, the envelopes may be reusable. The plates are put in the patient's mouth and exposed to X-rays. Upon exposure, the plates are taken out from the patient's mouth, envelopes are torn open, and the exposed plates proceed to scanning.

In one arrangement, the application software sends the scanner an instruction to reserve the scanner, so that only scanning of plates selected for the created study folder is conducted. The scanner receives the "to reserve scanner" instruction and is reserved for scanning. This step is designated as step 120 in FIG. 11.

With the scanner reserved, its LCD monitor displays reservation job details (such as patient identification information and the like). All other images scanned by the "reserved" scanner from the plates associated with the created study folder will refer to the same job. Thus, there is little likelihood of mismatch with plates assigned to the other study folder. It can be observed that where a single working station is provided with its own scanner (the "one to one" configuration), the scanner can remain in "Auto Reserved" mode and there is no need to reserve it.

The tagging device provided at the scanning station reads the data stored in the memory of the RFID tag and, in the event that this is the very first scan for this plate, it writes the scanning date in the tag's memory. When the date of the first scan is stored, it will not be updated subsequently.

The tagging device reads the current scan count value and increments it. Optionally, the tagging device may also compare the scan count value to a threshold count value and report a carrier plate whose scan count meets or exceeds the threshold count value, so that the reported carrier plate can be removed from service at an appropriate time. These steps are designated as steps 122 and 124.

In a step 126, the scanner reads patient identification data from the study folder, scans the plate, and displays the obtained image on the scanner's LCD monitor along with patient identification data. The displayed image can be a preview image, at reduced resolution, displayed within a template that is associated with the study folder, as described earlier. Eventually, in a step 128, the obtained image is stored as a DICOM file and is moved to the study folder. In a step 130, the study folder with the stored DICOM file passes to the processing and acquisition station. Here, the received DICOM file is processed, displayed on the screen of the working station, and sent to the database for archiving in a step 132.

After the plate is scanned and the image is obtained, the plate is erased and evacuated from the scanner. Then the plate is sealed in a disposable envelope to be ready for a new working cycle. After all plates have been scanned and all DICOM files have been acquired and archived, the application software issues the instruction "delete study folder" to the scanner. This is done in steps 134 and 136. Upon receipt of this instruction, the study folder is deleted from the scanner.

The software can issue an instruction to stop the reservation of the scanner (i.e., "unreserved scanner"). This instruction would be sent to the scanner. An unreserved scanner is noted in FIG. 11 at step 140.

The processing and acquisition process is completed.

Each plate can be identified in terms of its manufacturing date, size, first scanning date, and number of scanning cycles. With this arrangement, it is possible to monitor the plate's service life and to replace the plate when it becomes necessary.

Figure 12:
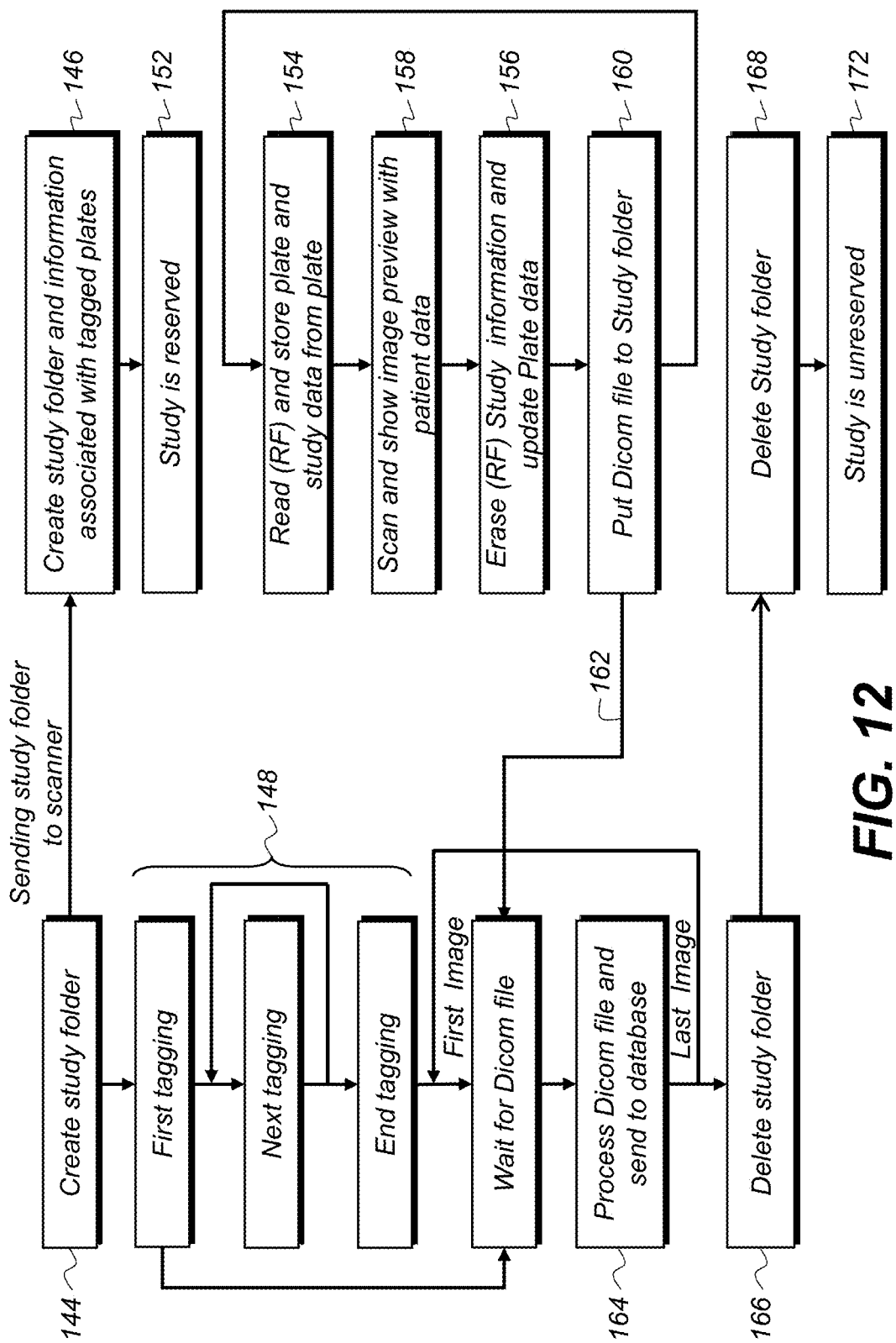
FIG. 12 is a block diagram of the working cycle shown in FIG. 5B.

The block diagram of FIG. 12 shows the interaction between processing and acquisition station and scanning station that takes place during computed intra-oral radiography in accordance with another embodiment of the present invention. FIG. 12 refers to a situation where there is a tagging device deployed both at the scanning station and at the working station.

In this situation, information carrier plates have RFID tags with memory that stores written permanent data 108 (manufacturing date and plate size), written-once data 110 (first scan date) and various types of dynamic data 112 (scan count and scan status, job number, resolution, destination address).

In the beginning of this working cycle, the processing and acquisition application software prepares the working cycle. In a step 144, a study folder is formed with patient identification information (patient data) and other previous treatment study data available from the database. The folder also indicates details of the current treatment, like tooth number, scan resolution, shot type (full mouth shot or single shot) and the like. Simultaneously with creation of the study folder, the software application issues a unique reference associated with this folder and with the required treatment. This reference or job number can be an assigned or a random number generated by the software itself or taken from the stored stock of random numbers. The study folder, along with the treatment details (job details), e.g. tooth number, scan resolution and the like is also sent to the scanner which receives it and temporarily stores it as designated by a step 146.

Then, in a step 148, tagging is initiated and the plates, enclosed in disposable envelopes, are sequentially tagged by the tagging device deployed at the working station. During tagging, the above mentioned dynamic information is written in the memory of the RFID tag. After the all plates have been tagged, they proceed to exposure to X-rays as explained in connection with the previous embodiment.

The exposed plates are extracted from the patient's mouth, their envelopes are torn open, and the plates proceed to a scanner in which the study folder, job details, and job number are stored. The software at the processing and acquisition station issues the instruction "reserve scanner". After the scanner is reserved, the first plate with RFID tag is inserted into the scanner. The tagging device at the scanning station reads dynamic information written in the memory of the RFID tag and increments the scan count, thus increasing the instant scan count. Furthermore, the plate is scanned at the resolution indicated in the dynamic data and the tagging device deletes the present job number. Furthermore, the tagging device updates the status of the plate to "scanned".

The obtained image is displayed on the scanner's LCD monitor along with patient identification data. The obtained image is stored in the study folder as a DICOM file with a header containing patient identification information, job details and job number. The sequence of processes for scanning, processing, and storing the obtained image is shown in steps 152, 154, 156, 158, and 160 of FIG. 12.

The processing and acquisition station waits until it receives the saved DICOM file for processing and display in an appropriate window on the template. Upon completing the acquisition, the DICOM file proceeds to the database for archiving. This sequence of events is designated by steps 162, 164 and it repeats with all plates that were tagged and scanned as part of the same examination session.

When the plate is scanned, it can be erased so that it is ready to proceed to the working station. Here, it is enclosed into a disposable envelope to be available for the new working cycle.

When the last DICOM file for an exam is archived, the software application deletes the created study folder from the processing and acquisition station, as well from the scanner. The acquisition step comes to its end and the scanner receives status "unreserved". This sequence is shown in steps 166, 168, and 172.

With this arrangement, wherein each carrier plate has an RFID tag immediately affixed to one side, it is always possible to identify, monitor, and track the plates during the entire working cycle, whether or not they are enclosed within the envelopes. Having the RFID tag applied to the plate can also help to assist in plate orientation, so that the exposure source is on the side of the phosphor coating, rather than on the opposite side that has the RFID tag. Because the RFID tag stores both permanent and temporary information, it is possible to unequivocally identify the plates during each part of the working cycle, whether or not the plates are scanned. This is possible because the RFID tag has a unique job number associated with the patient identification information and with job details.

Other benefits of the present invention that result from providing the RFID tag with both permanent and temporary information include the capability for monitoring plate service life by establishing manufacturing date, first activation date, and number of scanning cycles passed. Storing this data can help the user to monitor overall usage and manage plate allocation and replacement. In one embodiment, the scan count is checked at the beginning of each working cycle and, if appropriate, the Scan status field in memory is flagged as Past Useful Life or identified as Unusable.

The invention has been described in detail with particular reference to certain preferred embodiments thereof, but it will be understood that variations and modifications can be effected within the scope of the invention. For example, various types of data can be stored in the RFID tag or in the memory circuitry that is used by the interrogator.

Thus, there is provided a system and method for identification, monitoring, and tracking of flexible information carrier plates used in intra-oral dental computed radiography.

What is claimed is:

1. A method for obtaining an intra-oral X-ray image of a subject on a flexible information intra-oral carrier plate for computed radiography, comprising:
    affixing a memory to a surface of the information intra-oral carrier plate, wherein the affixed memory stores information about the information intra-oral carrier plate and wherein the affixed memory is in wireless communication with a computer;
    storing at least a first scan date in the affixed memory; and
    obtaining the intra-oral X-ray image of the subject by:
        (i) storing at least a job identifier and a scan status for the information intra-oral carrier plate in the affixed memory;
        (ii) acquiring image data from a scan of the flexible information intra-oral carrier plate following exposure to X-rays, acquiring at least the job identifier from the affixed memory, and associating the acquired image data with the acquired job identifier;
        (iii) incrementing a scan count value and updating the scan status in the affixed memory of the exposed flexible information intra-oral carrier plate;
        (iv) erasing image content from the flexible information intra-oral carrier plate; and
        (v) storing the acquired image data in a second, computer-accessible memory according to the acquired job identifier.

2. The method of claim 1 wherein obtaining the X-ray image further comprises storing a destination address for the acquired image data in the affixed memory.

3. The method of claim 1 wherein obtaining the X-ray image further comprises storing a resolution value for the obtained image in the affixed memory.

4. The method of claim 1 further comprising wirelessly tracking the use of the flexible information intra-oral carrier plate by checking the scan count.

5. The method of claim 1 wherein storing the job identifier further comprises associating the job identifier with a data field within an electronic template that comprises a plurality of data fields.

6. The method of claim 5 further comprising displaying the acquired image within the electronic template.

7. The method of claim 1 wherein obtaining the X-ray image further comprises associating the acquired image with an electronic study folder.

8. The method of claim 7 further comprising associating patient data with the study folder.

9. The method of claim 1 wherein acquiring the image data further comprises sending an instruction to reserve a scanner.

10. The method of claim 9 further comprising sending an instruction to un-reserve a scanner following acquisition of the image data.

11. The method of claim 1 wherein storing the acquired image comprises storing the image in DICOM format.

12. The method of claim 1 wherein storing the job identifier in the affixed memory further comprises obtaining data over a wireless network connection.

13. A method for tracking a plurality of flexible information intra-oral carrier plates having intra-oral dental images associated with a patient, comprising:
    affixing a memory to a surface of each of the flexible information intra-oral carrier plates, wherein the affixed memory is accessible using wireless communication and wherein the affixed memory stores at least a manufacturing date for the plate and provides storage for information related to a job;
    forming a study folder in a second, computer-accessible memory external to the information carrier plates, wherein the study folder is associated with the patient; and
    for each flexible information intra-oral carrier plate associated with the patient:
        (i) storing at least a job identifier and scan status for the flexible information intra-oral carrier plate in the affixed memory;
        (ii) acquiring image data from a scan of the flexible information intra-oral carrier plate following exposure to X-rays, acquiring at least the job identifier from the affixed memory, and associating the acquired image data with the acquired job identifier;
        (iii) incrementing a scan count value and updating the scan status in the affixed memory of the exposed flexible information intra-oral carrier plate;
        (iv) erasing image content from the flexible information intra-oral carrier plate; and
        (v) storing the acquired image in the study folder of the computer-accessible memory according to the job identifier.

14. The method of claim 13 further comprising associating the study folder with a displayed template of user images obtained for the patient.

15. The method of claim 13 further comprising comparing the scan count value to a threshold count value and reporting an intra-oral carrier plate whose scan count meets or exceeds the threshold count value.

16. A method for associating a plurality of images to a patient, comprising:
    affixing a memory to a surface of each of a plurality of flexible information intra-oral carrier plates, wherein the affixed memory stores at least a manufacturing date for the plate and provides storage for information related to patient images and wherein the affixed memory is accessible using wireless communication;

forming a study folder in a second computer-accessible memory external to the flexible information intra-oral carrier plates, wherein the study folder is associated with the patient; and for each of the plurality of flexible information intra-oral carrier plates:
  (i) storing at least a job identifier associated with the patient and scan status for the plate in the affixed memory using wireless communication;
  (ii) acquiring image data from a scan of the flexible information intra-oral carrier plate following exposure of the patient to X-rays;
  (iii) incrementing a scan count value and updating the scan status in the affixed memory of the exposed flexible information intra-oral carrier plate using wireless communication;
  (iv) erasing image content from the flexible information intra-oral carrier plate;
  (v) storing the acquired image in the study folder of the second computer-accessible memory according to the job identifier; and
  (vi) displaying image contents of the study folder of the second computer-accessible memory as part of a template.

17. The method of claim 16 wherein storing the job identifier further comprises associating the flexible information intra-oral carrier plate with a position in the template.

18. The method of claim 16 further comprising checking the scan count value to determine usage of the flexible information intra-oral carrier plate.

19. A system for obtaining an intra-oral X-ray of a patient, the system comprising:

one or more flexible information intra-oral computed radiography carrier plates, each information intra-oral computed radiography carrier plate having an affixed memory;

at least one processing and acquisition station in communication with a first wireless tagging device that is operable to read and write both permanent and amendable information into the affixed memory of the one or more information intra-oral carrier plates over a first wireless communication channel, wherein the amendable information comprises at least a job identifier and scan status for the information intra-oral carrier plate; and at least one scanner in communication with a second wireless tagging device that is operable to read and write both permanent and amendable information into the affixed memory over a second wireless communication channel, wherein the at least one scanner is actuable to obtain an image from each of the one or more flexible information intra-oral carrier plates, wherein the amendable information comprises at least a job identifier and scan status for the information carrier plate.

20. The system of claim 19 wherein the affixed memory is part of a radio-frequency identification device, and wherein the one or more information carrier plates are flexible intra-oral computed radiography information carrier plates, and wherein the amendable information in the at least one processing and acquisition station and/or the at least one scanner further comprises patient information and/or treatment study information.

\* \* \* \* \*